United States Patent [19]

Delson

[11] Patent Number: 5,513,654

[45] Date of Patent: May 7, 1996

[54] SLIP-RESISTANT CONTRACEPTIVE MALE CONDOM

[75] Inventor: David A. Delson, Seattle, Wash.

[73] Assignee: New Designs Corporation, Seattle, Wash.

[21] Appl. No.: 425,713

[22] Filed: Apr. 20, 1995

Related U.S. Application Data

[63] Continuation of Ser. No. 258,255, Jun. 10, 1994, abandoned.

[51] Int. Cl.$^6$ ............................................. A61F 6/04
[52] U.S. Cl. ....................... 128/844; 128/918; 427/2.3
[58] Field of Search ................................. 128/844, 847, 128/918; 427/2.3; 604/346, 347, 349

[56] References Cited

U.S. PATENT DOCUMENTS

| | | | |
|---|---|---|---|
| 2,348,773 | 5/1944 | Wyman | 128/844 |
| 3,495,589 | 2/1970 | Clement. | |
| 3,553,308 | 1/1971 | Kobayashi et al.. | |
| 3,648,700 | 3/1972 | Warner. | |
| 3,677,225 | 7/1972 | Czirely. | |
| 3,951,141 | 4/1976 | Kopelowicz. | |
| 4,100,309 | 7/1978 | Micklus et al. | 427/2.3 |
| 4,320,752 | 3/1982 | Comparetto. | |
| 4,354,494 | 10/1982 | Hogin. | |
| 4,475,910 | 10/1984 | Conway et al.. | |
| 4,536,179 | 8/1985 | Anderson et al. | 427/2.3 |
| 4,564,006 | 1/1986 | Pomeranz. | |
| 4,576,156 | 3/1986 | Dyck et al.. | |
| 4,589,873 | 5/1986 | Schwartz et al. | 427/2.3 |
| 4,684,490 | 8/1987 | Taller et al.. | |
| 4,726,359 | 2/1988 | Schroeder | 128/844 |
| 4,794,920 | 1/1989 | Robichaud. | |
| 4,821,742 | 4/1989 | Phelps, III. | |
| 4,829,991 | 5/1989 | Boeck. | |
| 4,844,986 | 7/1989 | Karakelle et al. | 427/2.3 |
| 4,852,586 | 8/1989 | Haines. | |
| 4,855,169 | 8/1989 | McGlothlin et al.. | |
| 4,863,449 | 9/1989 | Therriault et al.. | |
| 4,869,723 | 9/1989 | Harmon. | |
| 4,881,553 | 11/1989 | Grossman. | |
| 4,964,416 | 10/1990 | Foldesy et al. | 128/844 |
| 4,966,166 | 10/1990 | Leffler. | |
| 4,971,071 | 11/1990 | Johnson. | |
| 4,977,903 | 12/1990 | Haines. | |
| 5,010,871 | 4/1991 | Christina et al.. | |
| 5,027,831 | 7/1991 | Reddy. | |
| 5,069,227 | 12/1991 | Maronian | 427/2.3 |
| 5,082,004 | 1/1992 | Reddy. | |
| 5,102,405 | 4/1992 | Conway et al.. | |
| 5,110,621 | 5/1992 | Sudo et al. | 427/2.3 |
| 5,111,831 | 5/1992 | Foggia. | |
| 5,113,874 | 5/1992 | Maronian | 427/2.3 |
| 5,121,755 | 6/1992 | Hegedusch. | |
| 5,158,556 | 10/1992 | Starley. | |
| 5,163,449 | 11/1992 | van der Valk. | |
| 5,209,242 | 5/1993 | Shields et al. | 128/844 |
| 5,284,159 | 2/1994 | Wilk. | |
| 5,385,871 | 7/1994 | Reddy | 128/844 |

FOREIGN PATENT DOCUMENTS

| | | |
|---|---|---|
| 822876 | 11/1951 | Germany. |
| 1250553 | 10/1971 | United Kingdom. |
| 89/02256 | 3/1989 | WIPO. |

*Primary Examiner*—Sam Rimell
*Assistant Examiner*—Michael O'Neill

[57] ABSTRACT

The disclosed sheath-like contraceptive condom, even in a rolled-up condition suitable for packaging or use, has a high coefficient of friction on the surface that comes into contact with penile skin, particularly the portion of this surface contacting the glans and preferably also the shaft of the penis. The outer surface of the rolled condom, on the other hand, preferably has anti-blocking or release properties, so that it can be rolled up and unrolled without difficulty. The high coefficient of static friction (>0.70, preferably > about 1.0, according to ASTM Designation D 1894-90) on the interior surface provides reliable frictional engagement of at least the glans and preferably also the shaft of the penis, so that the condom clings to the contours of the penis and resists slippage during intercourse.

27 Claims, 1 Drawing Sheet

U.S. Patent     May 7, 1996     5,513,654
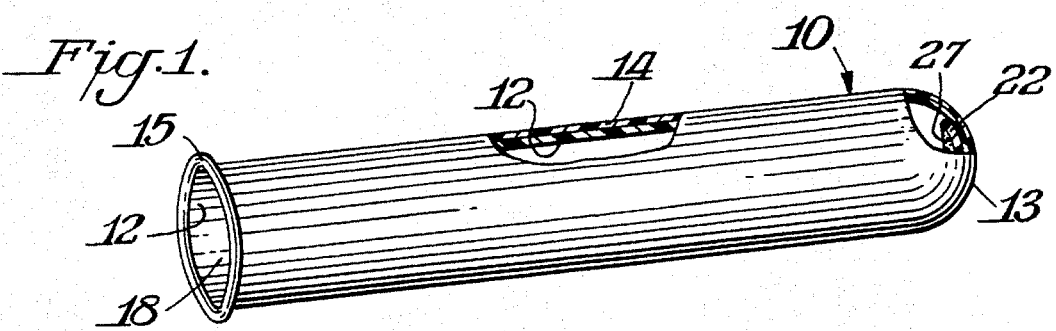
Fig. 1.
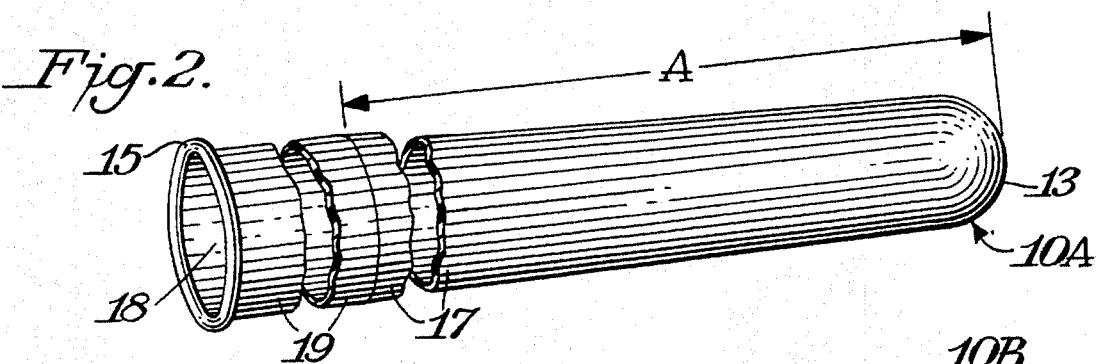
Fig. 2.
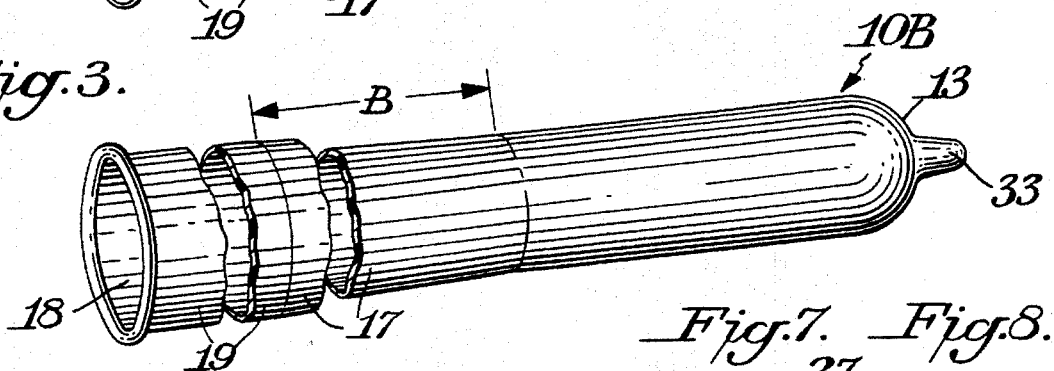
Fig. 3.
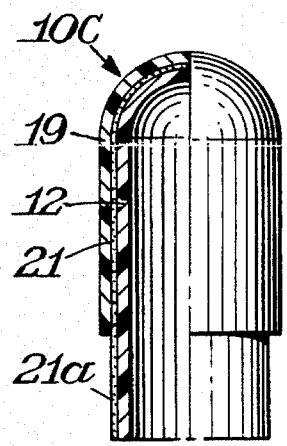
Fig. 4.
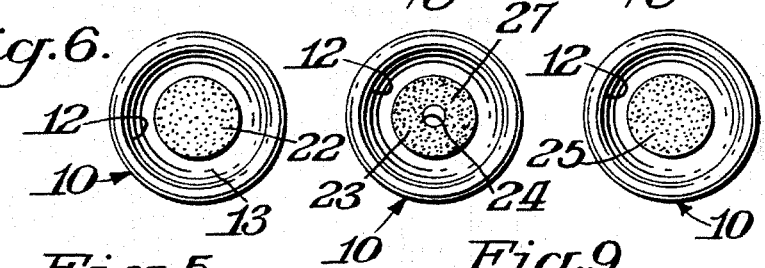
Fig. 6.    Fig. 7.    Fig. 8.
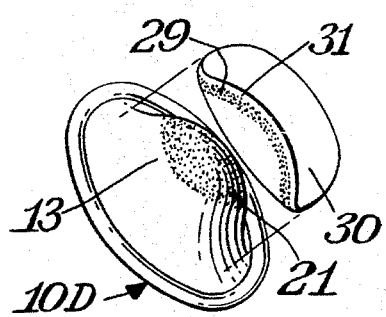
Fig. 5.
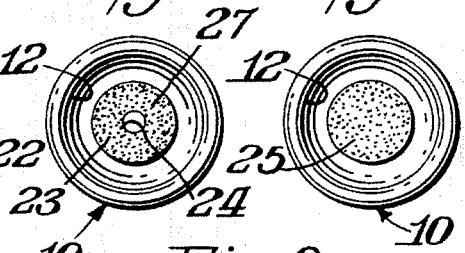
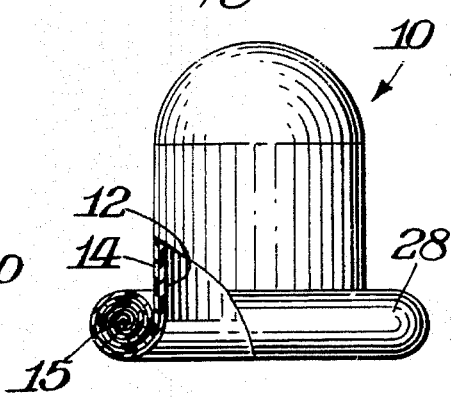
Fig. 9.

SLIP-RESISTANT CONTRACEPTIVE MALE CONDOM

This is a continuation of my application Ser. No. 08/258,255, filed Jun. 10, 1994, now abandoned.

FIELD OF THE INVENTION

This invention relates to a male condom or prophylactic device which is to be used for preventing human conception and the transmission of infection, disease, and general contamination caused by exposure of a male sexual organ to a contaminated or problematic environment. Other aspects of this invention relate to methods for making and using the condom.

DESCRIPTION OF THE PRIOR ART

It is likely that some form of contraceptive has been employed by man since prehistoric times. There is evidence that the ancient Greeks, Romans, and Egyptians used oiled animal bladders and lengths of intestines as sheaths, most probably for preventing both conception and disease. In some respects, even the most modern of condoms share some common features with these very ancient contraception and disease prevention devices, but the use of elastomers (e.g., natural or synthetic rubber sheaths, typically formed from latices) in modern times has opened the door to a variety of condom design concepts. Thus, while animal skin condoms are still commercially available, and synthetic elastomers are beginning to be introduced into the commercial marketplace, much of the patent literature is concerned with rubber latex sheaths.

Although vulcanization of rubber has been known since the early 1840's, vulcanized rubber was not perfected as a means of condom manufacture until many decades after its discovery. By converting natural rubber from a generally linear polymer to a highly crosslinked material, vulcanization lowers the brittleness temperature; raises the tensile stress at significant elongations (e.g., 50–100%); raises the tensile strength of rubber to well over 1000 pounds per square inch, i.e., > about 7 megapascals (mPa), typically to >20 mPa; improves resistance to degradation at temperatures of >40° C.; improves elongation to at least 500%, more typically >600%, and thereby makes possible a relatively safe (breakage-resistant) but relatively thin (and hence disposable) condom, e.g., a condom with wall-thicknesses in the range of about 1 to 6 mils or about 0.03 to 0.15 millimeters (mm), more typically about 0.05 to 0.10 mm. Vulcanized natural rubber tensile strengths above 25 mPa are readily achieved and can be superior to tensile strengths of synthetic polymers, although excellent physical properties are also obtainable with modern synthetic polymers (e.g., elastomeric polyurethanes which can, if desired, be highly crosslinked). Today, vulcanization can be effected either before or after a natural rubber latex is formed into a sheet (rubber which has been vulcanized while still in a particulate state is often referred to as "prevulcanized"). Thus, modern rubber technology offers the condom designer a range of possibilities which were unknown in this field as recently as the 1920's.

According to the patent literature, modern condom design trends relate not only to barriers for the prevention of conception and disease transmission, but also to catheters for urine collection. It presently appears that most if not all elastomeric condom structures described in the patent literature are intended to achieve some sort of sealant or engagement relationship with the human penis (e.g., to prevent spillage of semen), but the approaches to this broad objective vary significantly. In some structures the emphasis is on engagement of a portion of the shaft of the penis (particularly at or near its proximal end), while in others the emphasis is on engagement along most if not all of the length of the penis. Frictional engagement of penile skin has long been considered an important aspect of condom design, but it also has been assumed that frictional engagement alone is insufficient and must be supplemented in a very substantial way by other engagement and/or sealant means or principles, including elastic tension (natural and synthetic latex rubber as well as other elastomers can have sufficient elastic and/or tensile moduli for this purpose), a pressure-sensitive adhesive layer on some part of the interior of the condom sheath, and even mechanical retention means such as constrictive bands, straps, and the like.

There are other aspects of condom structure and function which can diverge radically. For example, according to the so-called "form-fitting" design concept, there is an attempt to minimize slippage of the penis within the interior of the sheath, although some slippage of the head or glans (distal end) of the penis relative to the interior of the sheath is difficult to prevent entirely. Stimulation of a penis covered by a form-fit condom is obtained in essentially the same manner as in coitus carried out with no disease or conception barrier, i.e., through sliding contact with the interior of the vagina, hence it is generally desirable to minimize the thickness of a form-fit sheath. But according to a wholly different, non-form-fitting design concept, stimulation of a penis is provided by sliding contact between the penile skin (particularly the glans) and the interior of the sheath; in this case, the sheath can be relatively thick, but the mechanism of stimulation of the penis differs sharply from the natural mechanism and, to prevent spilling of ejaculate, a high degree of constriction of the sheath near the proximal end of the penis is often required. In some especially oversized embodiments of the non-form-fitting design concept, the exterior of the condom sheath is intended to engage the interior of the vagina in a manner which inhibits movement of the condom sheath while permitting relatively free sliding movement of the penis within the interior of the sheath. An internal lubricant is typically provided within the sheath to further facilitate such sliding movements (rather than minimize them, as in the case of form-fit condoms).

Representative examples of non-form-fitting or loose-fitting designs are described in Brook, WIPO (PCT) publication WO 89/02256 (1989), U.S. Pat. No. 4,869,723 (1989 to Harmon); British patent 1,250,553 (1971 to Richardson); and U.S. Pat. Nos. 4,966,166 (1990 to Leffler) and 5,027,831 and 5,082,004 (1991 and 1992, respectively, to Reddy). A "semi-form fitting" concept is described in U.S. Pat. No. 5,163,449 (1992 to van der Valk). So-called female condoms typically are sheaths designed to utilize some of the principles of loose, oversized (non-form-fitting) male sheaths. Perhaps the most fundamental difference between male form-fit condoms and female condoms (or even oversized male condoms) lies in the human anatomy they are designed to engage: form-fit male condoms are essentially intended to engage a penis, while female condoms typically engage or become anchored to either the vagina or the cervix, and loose, oversized male condoms also rely to some degree on vaginal engagement.

A condom which does not engage the penis can be provided with a proximally extending flange (extending distally from the vagina). This flange has been proposed for the purpose of keeping the open end of the sheath outside the woman's body during coitus. See U.S. Pat. No. 4,794,920 (1989 to Robichaud).

When a condom structure is intended to be form-fitting and to make use of the elastic modulus of natural or synthetic latex rubbers or other elastomers to provide elastic-tension engagement of the penis, the width or diameter dimension of a generally tubular sheath configuration typically will be more-or-less constant throughout the axial length. This dimension is ordinarily intended to be based upon the median circumference of an erect human penis. Throughout most of the world and over many decades the diameter dimension selected by most condom designers has been within the range of about 32–35 millimeters. More recently a second diametric range of 29–33 millimeters has been introduced into the Asian markets. These dimensions are understood to allow for approximately a 15% expansion over the median circumference of an erect human penis. The elastic tension resulting from this expansion is intended to hold the condom in place during intercourse.

Some condom designers have suggested the use of relatively higher-modulus, non-latex elastomers. Representative examples of such suggestions can be found in U.S. Pat. Nos. 3,553,308 (1971 to Kobayashi); 4,576,156 (1986 to Dyck); 4,684,490 (1987 to Taller); and 4,855,169 (1989 to McGlothin).

Representative examples of disclosures of mechanical means to secure the condom to a penis can be found in U.S. Pat. Nos. 3,495,589 (1970 to Clement), 4,354,494 (1982 to Hogin); 4,971,071 (1990 to Johnson); 5,010,871 (1991 to Christina); 5,111,831 (1992 to Foggia); 5,121,755 (1992 to Hegedusch); and 5,158,556 (1992 to Starley). U.S. Pat. No. 4,564,006 (1986 to Pomeranz), shows a slide fastener closure device aiding the placement of the condom upon a flaccid penis.

German patent 822,876 (1949 to Wendt) as well as U.S. Pat. Nos. 3,648,700 (1972 to Warner); 3,677,225 (1972 to Czirely); 3,951,141 (1976 to Kopelowicz); 4,320,752 (1982 to Comparetto); 4,475,910 (1984 to Conway et al); 4,821,742 (1989 to Phelps); 4,863,449 (1989 to Therriault et al); 4,869,723 (1989 to Harmon); and 5,102,405 (1992 to Conway) disclose condoms which utilize pressure-sensitive adhesive as a means of preventing the condom from slipping off of a penis and/or preventing spillage following ejaculation. Because it comes into direct contact with skin, the adhesive is normally a medically-approved type such as a hypoallergenic acrylic pressure-sensitive adhesive (see Therriault et al, U.S. Pat. No. 4,863,449, column 4, lines 35 to 39).

It has been proposed that a condom may be folded rather than rolled, e.g. the Fourex® condom manufactured by Schmid Laboratories. Most manufacturers of male condoms would be likely to reject such a proposal, and many experts in the field of male condom design consider condom rolling to be an indispensable aspect of condom manufacture and usage. For an example of a condom designed to be folded see U.S. Pat. No. 4,829,991 (1989 to Boeck).

The design of condom structure and function is generally intended to satisfy, as much as possible, a diverse set of criteria including comfort for the wearer (preferably when the penis is either flaccid or erect), maximum stimulation of both male and female genitalia, ease of application to a penis (again, preferably regardless of whether the penis is erect or flaccid), safety (resistance to breakage), ease of removal after intercourse, and prevention of spillage of semen. Some of these criteria appear to impose mutually exclusive design requirements and thereby create serious trade-off problems.

For example, among the more elusive goals of elastomeric, form-fitting condom design are complete retention of the condom upon a penis so that spillage does not occur following ejaculation, and prevention of slippage of the condom against the penile skin during intercourse. To avoid creating excessive discomfort for the condom wearer, the elastic tension provided by sheaths manufactured from typically-used types of rubber latex does not ordinarily result in a grip on the glans or shaft of a human penis which is firm enough to prevent either slippage of the penis with respect to the interior of the sheath, or a bunching-up of material at some point along the length of the condom. If the elastic tension is increased by reducing the diameter of the sheath or increasing the modulus of the rubber, excessive constriction of an erect penis can occur.

Mechanical means of engagement are cumbersome, and the use of pressure-sensitive adhesive which comes into direct contact with a portion of the glans or shaft of a penis can have the undesired effect of inhibiting removal of the condom after intercourse, since pressure-sensitive adhesive bonds to skin resist 90°-peel and 180°-peel forces (as is familiar to anyone who has removed pressure-sensitive adhesive surgical tape or bandages from human skin).

For additional illustrations of the condom art, see U.S. Pat. Nos. 4,852,586 (1989 to Haines); 4,977,903 (1990 to Haines); 4,881,553 (1989 to Grossman); and 5,284,159 (1994 to Wilk). For an interesting illustration of sheath shapes selected from a different art (finger cots or sheaths), see U.S. Pat. No. 2,348,773 (1944 to Wyman).

Elastomeric, sheath-type condoms can be manufactured through the use of a variety of techniques, the most widely used technique being the dip-molding process, wherein a core or mandrel is dipped in a liquid-state dipping solution. The core becomes covered with a thin film of polymer which can, if desired, be further coalesced and/or cross-linked or vulcanized with heat or chemical treatments. The resulting sheath structure is then stripped from the core by rolling it up outwardly upon itself or, alternatively, by "wet-stripping" the condom from the core, a process well known to those skilled in the art of condom manufacture.

Handling of freshly-formed sheaths (e.g., stripping from the core, storage and packaging of completed condoms, etc.) can be complicated somewhat by film-to-film adherence effects as in the blocking of plastic films. Natural rubber latex films, for example, have extremely strong blocking tendencies, to the extent that two thin natural rubber latex surfaces placed in contact with each other would be extremely difficult if not impossible to separate. Traditionally, an anti-blocking, friction-reducing material or "dressing agent" (a dusting powder or lubricant or a combination thereof) is applied to both the exterior and interior surfaces of the sheath prior to or during removal from the core or prior to rolling up of the sheath. Typical dusting agents include talc, calcium carbonate, silica, lycopodium, corn or potato starch, or the like, or combinations thereof.

The present invention seeks to provide a contraceptive condom (preferably a full-length, form-fitting male condom) which is: comfortable to wear (on either an erect or a flaccid penis), breakage and spillage resistant, easily donned (regardless of whether the penis is erect or flaccid), and strongly resistant to slippage even during vigorous coitus, but does not require folding instead of rolling and can, if desired, be manufactured without radical departures from conventional manufacturing techniques and can, if desired, be made in the usual form-fitting male condom thicknesses or even thinner, from any polymer possessing suitable properties including vulcanized or pre-vulcanized natural rubber.

SUMMARY OF THE INVENTION

In the manufacture of a contraceptive condom of this invention, the material from which the sheath is made is selected to provide a high coefficient of friction, at least on the interior surfaces of the glans-enveloping portion of the sheath (typically the most distal one-fourth to one-third of a full-length sheath), the objective of this high coefficient of friction being a high degree of frictional engagement of a substantial portion of the distal penis, and preferably the proximal penis as well. For the sake of simplicity, it is preferred that the high coefficient of friction be inherent in the sheath material rather than the result of introducing a friction-enhancing material onto the aforementioned interior surfaces, and enhancement of the coefficient of friction by means of adhesive materials is particularly undesirable in the context of this invention. Since conventional condom dressing agents can have friction-reducing as well as anti-blocking properties, dressing agents are substantially not present on the interior condom surfaces at least insofar as the distal, glans-enveloping portion is concerned.

Alternatively, the surface of the dipping mandrel can be patterned or inscribed in such a manner so that, when removed from the mandrel, the interior surfaces of the condom demonstrate a high coefficient of friction, even if that property is not inherent in the sheath material. However, condoms with generally smooth interior surfaces comprised of inherently high-friction material are preferred.

To simplify manufacturing, handling, and particularly unrolling of a rolled-up condom of this invention, the exterior surfaces of the condom are substantially non-blocking (i.e., have release characteristics).

When the static coefficient of friction of the interior portion of the sheath is measured in accordance with A.S.T.M. Designation D 1894-90, values in excess of about 0.70, preferably >1.0 (e.g., about 1.3 and up to about 2.0 or more) are normally obtained, as compared to <0.55 for a sheath interior provided with a conventional dressing agent. These higher ASTM D 1894-90 values have been found to correlate with significantly improved slip-resistant effects, without the need for any increase in the elastic tension exerted by the stretching of the sheath by an erect human penis—indeed, with little or no contribution to slip-resistance from elastic tension. Accordingly, the diameter and/or tensile modulus of the sheath can be selected for maximum comfort on both erect and flaccid penises, if desired.

A contraceptive male condom of this invention is preferably of the full-length type which covers the glans and all or most of the shaft of a human penis. This condom normally will cling to the contours of a human penis (particularly the contours of the glans and at least a portion of the shaft), but generally as a result of frictional forces, elastic tension principally not being required. The rolled condom when ready for packaging or for use during intercourse comprises:

a thin-walled (<0.09 mm, preferably <0.05 mm, in thickness) sheath having, when unrolled, a generally hemispherical closed or distal end, the sheath being generally tubular except for the closed end, a generally tubular distal portion extending proximally from, but not including, said closed end, and an open or proximal end, the distal portion extending proximally a sufficient part of the length of said sheath (e.g., >25%, preferably >50%) to surround the glans of an erect human penis and to frictionally engage the glans, especially during intercourse; this sheath in its packaged or ready-to-use condition is rolled up outwardly upon itself (resulting in convoluted edges having as many convolutions as needed to roll up at least most of the length of the sheath), and the interior surfaces of the generally tubular distal portion are substantially free of measurable tack at normal and slightly elevated ambient temperatures (up to at least 40° C., preferably up to at least 50° C.) and have a static coefficient of friction, determined in accordance with A.S.T.M. Designation D 1894-90, of greater than about 0.70, preferably >1.0, even after the condom has been rolled up for packaging. Preferably, as indicated above, the exterior surface of the distal portion has anti-blocking (release) characteristics. Thus, a particularly preferred condom of this invention has a high coefficient of friction on the inside, causing it to cling to penile skin and contours and be slip-resistant, but is still non-blocking (and preferably lubricious) on the outside. However, the penile skin in contact with the generally tubular distal portion preferably does not encounter significant peel resistance when the condom is removed.

BRIEF DESCRIPTION OF THE DRAWING

FIG. 1 is a perspective view partially broken away of a preferred embodiment of the invention illustrating the combination of a slip-resistant interior surface, an outermost release (anti-blocking) layer, and details of the structure of the closed end of this embodiment.

FIG. 2 is a perspective view of a further embodiment of the invention illustrating the use of an increase in diameter toward the open end which defines a gradual taper along a substantial portion of the axial length of the contraceptive sheath.

FIG. 3 is a perspective view of still another embodiment of the invention illustrating the use of an increase in diameter toward the open end of the sheath which defines a substantially frusto-conical-shaped section extending along a portion of the axial length of the condom.

FIG. 4 is a fragmentary side elevational view, partially broken away to reveal details of the structure of still another embodiment of the invention illustrating the use of a lubricant or other fluid material which is protected from transfer to the interior surfaces of the sheath during manufacture by an outer protective film covering the distal portion of the sheath.

FIG. 5 is a perspective view of yet another embodiment of the invention illustrating the use of a secondary film layer which adhesively affixes to the exterior tip of the distal portion of the sheath, between which secondary layer and the condom sheath is disposed a lubricant or other fluid.

FIG. 6 is a left end-elevational view (i.e., a view through the opening) of the embodiment of FIG. 1.

FIG. 7 is a left end-elevational view, similar to that of FIG. 6, of a modification of the embodiment shown in FIG. 6.

FIG. 8 is a left end-elevational view, similar to that of FIGS. 6 and 7, of another modification of the embodiment shown in FIG. 6.

FIG. 9 is an enlarged side elevational view, partially broken away, of the embodiment of FIG. 1 in a rolled up condition, showing details of the structure and the convolutions formed by the rim which has been rolled up outwardly.

DETAILED DESCRIPTION OF THE PREFERRED EMBODIMENTS

As indicated above, the present invention seeks to provide a condom which resists slippage on the penis, due to frictional engagement of at least the distal penis (e.g., at least the glans), even during vigorous intercourse. Elastic tension (obtained either by selecting a diameter which requires expansion to fit an erect, adult human penis and/or by selecting an appropriately elastic sheath material) can if desired be employed to enhance slip resistance during intercourse, but elastic tension is not a principal requirement of this invention, and any amount of elastic tension which would cause discomfort to the wearer is preferably avoided.

It has been found that a substantially exclusively frictional engagement of at least the distal penis (and preferably the proximal penis as well) not only provides greater comfort to the wearer as compared to other forms of engagement, but also strongly inhibits spillage of semen and slippage of the condom on the penis during intercourse (or when the penis is in a flaccid state).

Additional objectives of the invention are to provide a condom which:

1) Does not interrupt lovemaking: The present device can be worn for an extended period of time prior to intercourse either on a flaccid or erect penis, thus making it possible to avoid interruption in lovemaking.
2) May be placed upon a flaccid penis: The present device can be applied to a flaccid penis and, due to its slip-resistant interior surface, worn in that state prior to erection without loss of adhesion to penile skin which could cause the condom to slip off.
3) Is more easily donned on an erect penis: Typically, as a conventional lubricated or dusted condom is donned, that portion of the condom which has been unrolled tends to detach easily or pull away from the penile skin due to the low coefficient of friction which exists between the penile skin and the interior condom surface. As the condom is donned, there is a tendency for the fingers to pull the loose, most recently unrolled portion of the condom into the adjacent rolled-up portion (the annular ring of rolled convolutions) which is being further unrolled, thereby interfering with the unrolling of the sheath. This is particularly true as the rolled-up portion of the condom becomes smaller as the condom is further unrolled along the penile shaft. The slip-resistant interior surface of the inventive condom tends to grip the penile skin as the sheath is unrolled, thereby greatly reducing this tendency of the fingers to pull the unrolled portion of the condom sheath into the annular ring of rolled convolutions.
4) Provides increased sensation relative to form-fitting condoms with poor slip resistance: Because a condom of this invention can adhere to the glans and preferably also the shaft due to frictional effects, the tactile relationship between a penis protected by a condom of this invention and a vagina can more closely approximate the physical experience which occurs when no barrier is present. There is reduced movement of a penis within the sheath itself, thus eliminating the unpleasant sensation of a "bunching up" and/or creasing of material, as well as possible penile and vaginal chaffing.
5) Does not require prompt withdrawal: Spillage does not occur due to the secure but comfortable fit which results from the aforementioned frictional engagement.
6) Is resistant to breakage: The barrier film or condom sheath of devices incapable of frictional engagement of a penis are subject to substantial flexing and bending frictional stresses during intercourse, whereas the film of the present device is subject to far less stress due to the contour-assuming characteristic of the slip-resistant interior surface, resulting in a reduced incidence of breakage, even at the very low thicknesses which are preferred for maximum transmission of sensations from vaginal walls to penile skin.
7) Is not adversely affected by vigorous lovemaking: The condom of this invention does not slip or separate from a penis even under conditions of vigorous lovemaking.
8) May optionally have a longer axial length than commercially-available condoms, without sacrificing comfort: Commercially-available condoms define a generally constant, tubular diameter throughout the axial length, and are sized to accommodate the "average" length of an erect penis. When such a condom is worn upon an erect penis which is shorter in length than a fully unrolled condom sheath, a painful constriction can occur at the base of the penis due to the resulting larger annular ring of rolled convolutions (i.e., a greater number of rolls). Preferred embodiments of this invention optionally may be provided with a longer axial length than has been possible heretofore as the result of an increase in the diameter toward the open end of the condom, thereby increasing the diameter of the annular ring of rolled convolutions, hence eliminating penile constriction. Therefore, a greater diversity of penile lengths may be accommodated comfortable. Additionally, the larger annular ring of rolled convolutions associated with a condom having a longer axial length facilitates donning of the condom by providing additional surface area to be contacted by the fingers.

In a preferred embodiment of this invention, the coefficient of friction of the material which comprises the initial dip coat onto the condom-shaped dipping mandrel defines the coefficient of friction being sought upon about 25 to 100%, preferably at least 50%, of the interior surface of the condom. This approach to providing a condom which clings to a penis by frictional engagement would appear at first glance to be highly problematic in its manufacture, storage, handling, and unrolling from the rolled state, due to the strong blocking tendencies of many types of latex rubber, synthetic elastomers, and other types of polymeric film. Accordingly, the film-forming material from which a condom of this invention is made is preferably (a) selected for high friction, but low blocking properties or, (b) if this material has blocking properties equal or similar to the conventionally-used natural rubber materials, at least part of the outer surface of the condom sheath is provided with sufficient release characteristics to facilitate rolling up and unrolling of the sheath. For example, some or all of the outer surface of the sheath can be coated or laminated with a film or layer of substantially non-blocking material, or physically or chemically modified to reduce blocking tendencies. An advantage of solid, well-anchored non-blocking or low-blocking materials (e.g., a solid, cured-in-situ coating or lamina) and some chemical and physical treatments is that they are localized; that is, the anti-blocking effects are non-transferable to inner surfaces and, even if these effects are also friction-reducing, they will not lower the high coefficient of friction on the interior surface or surfaces of the condom sheath. In any event, when the condom is stripped from the core or rolled up for storage in the usual manner, it is preferred that the exterior surface of the condom function as a release liner or low-adhesion back-size for the convolutions of the rolled rim, so that blocking of convolutions one upon the other is sharply reduced or eliminated.

As the condom of this invention is unrolled onto a penis in the typical fashion, it can be held in place by elastic tension, if desired, but this invention relies generally upon essentially non-adhesive but slip-resistant interior surfaces to provide frictional adherence to penile skin and, if desired, close conformity to the specific topological contours of a penis. When a condom of this invention has been completely rolled onto a penis and is frictionally engaged with penile skin, the penis has the appearance of being "shrink-wrapped."

Condom sheaths of this invention, in the rolled-up state, ready for packaging or for application to a penis thus have the aforementioned high coefficient of friction on their internal surfaces. The outer surfaces, on the other hand, are preferably substantially free of blocking tendencies, due to the selection or treatment of the material from which the sheath is made, but anti-blocking agents or treatments or the like are not permitted to reduce friction on the interior surfaces after the condom has been rolled up and is ready for packaging or use.

Condoms of this invention can be manufactured using a variety of techniques, including dip-molding (dip-coating), spray-forming, vacuum-forming, heat sealing, and blow-molding, the ordinarily preferred technique being a modification of conventional dip-coating, since most condom manufacturing facilities utilize dip-coating equipment.

The basic principles of the method of manufacture having the greatest simplicity are described in Conway et al, U.S. Pat. No. 4,475,910, FIG. 4 of the drawing, and column 2, lines 36 to 46 and column 4, lines 10 to 31 and in Okamoto, British patent 938,465, page 1, lines 11 to 16, except that the pressure-sensitive adhesive application step of the Conway et al disclosure is omitted. Briefly, this simple method involves dipping of a former (i.e., a core or mandrel) into a liquid-state material such as a natural or synthetic rubber latex, a cross-linkable or chain-extendible monomer or prepolymer, or a solution of a generally linear polymer. The freshly-dipped core or mandrel is then subjected to one or more solidification steps, e.g., solvent or carrier removal, coalescence, crosslinking, chain-extension, or any practical combination of these steps. The dipping/solidification sequence can be repeated as many times as desired to build up the desired thickness of sheath material deposited on the core or mandrel. The result is a sheath-like structure having a closed end supported by the end of the core and an open end or rim displaced some distance from the closed end.

A liquid-state release material is then applied to the outer surface of the solidified sheath material, and the coating (generally a very thin coating) of release material can be solidified by any of the solidification steps mentioned above, e.g., by "curing" (typically a combination of chain-extension, crosslinking, and chain-capping). As pointed out in U.S. Pat. No. 4,475,910, the liquid-state release material can be a curable silicone (polysiloxane) which forms, upon curing, a thin silicone layer with good lubricity and anti-blocking characteristics. The sheath is then stripped from the core. The sheath can be wet-stripped, so long as the interior surfaces of the wet-stripped sheath do not stick to each other in a manner which would interfere with subsequent handling of the sheath (e.g., the conventional roll-up step). Blocking of internal surfaces can be avoided by dry-stripping, wherein the freshly-formed sheath is rolled from its rim (open end) outwardly upon itself toward the closed end. During dry-stripping the thin, adhered layer of silicone does not transfer to the interior surfaces. Regardless of the stripping method employed, the ultimate result is a rolled-up condom which can be packaged in the conventional manner.

When the rolled-up sheath is unrolled (e.g., prior to intercourse), the thin layer of silicone acts much like a release liner or the low-adhesion back-size of a tape roll, hence unrolling can proceed easily.

Since some condom manufacturing processes already include a plurality of dipping steps, an alternative method of providing an anti-blocking release layer on the exterior surfaces of the condoms would simply involve, as indicated earlier, the selection of a film-forming material with inherent anti-blocking tendencies. If this film-forming material is used in all dipping steps, it would preferably also have a high coefficient of friction, but if it is used only in the last dip, high-friction characteristics are not required and low-friction characteristics can even be appropriate.

Alternatively, the outer surface of the freshly-formed sheath can be treated with a suitably localized physical or chemical treatment (a physical or chemical treatment which does not penetrate the thickness of the sheath). A second alternative method involves treating some or all of the outer surface of the freshly-formed sheath with a liquid or soft solid or particulate friction-reducing agent, then superposing over the treated area a very slightly oversized, generally conforming film in the shape of a cap which rolls up with the basic sheath structure but which is easily removed after the sheath is unrolled onto a penis. As explained subsequently, this second alternative can be used to provide a pre-lubricated condom which still retains the high coefficient of friction on internal surfaces, as provided in this invention.

The film- or sheet-like material selected for the basic condom sheath of this invention (i.e., the sheath minus any further film coatings for enhanced friction on the inside or enhanced lubricity on the outside) is preferably suitable for use in a dip-molding process and is preferably capable of forming high-strength films no greater than about 0.15 mm in thickness which are generally free of imperfections and have a tensile strength of at least about 15 mPa, more preferably >20 mPa. It is desirable that the material be generally free of surface tack at normal ambient and at moderately elevated temperatures.

Thus, a suitable sheath material can be a synthetic linear or cross-linked polymer or a fluid film-forming material such as a latex, curable prepolymer, or curable monomer. In its solid (coalesced and/or cured) form, the film can be elastomeric (as defined by ASTM D 1566, i.e., can be extended some multiple of its original length without any significant amount of permanent set) or non-elastomeric. Non-elastomeric films used to make condom sheaths of this invention are preferably flexible and capable of some degree of extension with minimal to modest permanent set. High-modulus films are not required and can even be undesirable but may be utilized, so long as the film has physical properties which render it resistant to breakage.

Thus, this basic sheath material can, if desired, be formed from natural or synthetic rubber latices, synthetic polyisoprene, polyurethane, polyurethane-urea, poly (siloxane urethane/urethane-urea) copolymers, poly(1,4 diene-vinyl aryl) random and block copolymers, or other suitable polymeric materials capable of forming films. Natural rubber latex is desirable in terms of its strength, modulus, extensibility, etc., its ready availability (particularly in the condom industry), and its high coefficient of friction at the surface, but it has a well-known tendency to be attacked by some lubricants, and can form pinhole flaws during condom manufacture; accordingly, synthetic elastomers and other synthetic polymers are of interest from the standpoint of safety, if for no other reason. The presently preferred sheath material for manufacturing a condom of this invention comprises a polyurethane, polyurethane-urea, or poly(siloxane urethane/urethane-urea) copolymer.

Other properties of importance in the case of the basic sheath material and coatings on this material as well include biocompatibility, hypoallergenicity or insensitivity to skin, chemical compatibility with subsequent dip-coats, and various physical properties (tensile modulus, flexural modulus, etc.) The high coefficient of friction, which is desirable for the reasons discussed previously, should be distinguished from surface tack or probe tack or pressure-sensitive adhesive tack, which is not desired. Blocking tendencies are also not desirable, but are generally difficult to avoid when a high coefficient of friction is desired. On the other hand, blocking tendencies can be reduced or eliminated by means of one or more of the previously mentioned techniques, described further below. Materials with suitable release characteristics for use as the outermost coating of condoms of this invention can be formulated using solid or liquid, reactive or non-reactive additives such as organic polymers with release properties (e.g., a polysiloxane such as a silicone film, a fluorinated polymer such as polytetrafluoroethylene, polyhexafluoropropene, and their partially chlorinated analogs and copolymers, and similar homopolymers and copolymers) or hydrogel coatings such as those used to coat Foley catheters, enteric feeding tubes, and the like, and practical combinations of these materials. An appropriate release characteristic can also be obtained by modification of the outermost surface of the condom by means of chemical treatment, gas plasma treatment, ion beam treatment, vapor deposition techniques or other surface modification technology which is practical for use under condom manufacturing conditions, which does not detract significantly from the safety of the condom as a disease and semen barrier, does not increase allergenic properties or decrease biocompatibility, and which does not penetrate the thickness of the sheath. One advantage of these surface-modification techniques is their effects are inherently localized and hence ideally suited to the simple method of manufacture described above. That is, even after carrying out an outward rim-rolling step, the frictional engagement properties of the interior surfaces remain unmodified. Similarly, treatment with a film or layer of material which can be anchored to the outer surface, chemically (e.g., with intermolecular cross-linking or with difunctional or other polyfunctional coreactants) or physically (e.g., by partial penetration of the outer surface), can produce an outer anti-blocking layer which resists transfer to the interior surfaces, as described above.

The desired anti-blocking coating or surface modification of the exterior surfaces of the condom can have the effect of increasing lubricity and reducing frictional effects, particularly as compared to the interior surfaces which are selected or treated to provide frictional engagement of skin. Increased lubricity on these exterior surfaces is not required but is desirable, since it facilitates entry of the penis into the vagina and also facilitates subsequent coitus. With appropriate surface treatments or highly specialized lubricants, the static coefficient of friction on outer surfaces can be well below 0.70, or even less than 0.10 (e.g., about 0.05).

Liquid or solid friction-reducing agents used to provide anti-blocking or release characteristics on the outer surfaces of the sheath preferably do not degrade the physical properties of the sheath polymer. Solid anti-blocking agents can be solid when applied or can be applied as a monomer, prepolymer, solution, emulsion, or the like, as described above.

It is well-known in the industry that a pre-lubricated condom (i.e., a packaged, rolled-up condom which already has lubricant on its exterior surfaces) is usually the consumer's product of choice. The aforementioned removable cap method for preventing transfer of the anti-blocking agent can be used to provide a pre-lubricated and/or spermicide-treated condom; that is, after the desired lubricant, biocide, and/or medicament substance or substances have been applied to the freshly-formed sheath, the cap-like, thin, readily removable outer or secondary film layer is superposed over at least the closed end or glans-enveloping portion of the condom, typically the distal third or distal fourth of the length of the full-length condom. The lubricant, spermicide or other biocide, and/or medicament is thereby sealed between the secondary film layer and the condom prior to roll-up and thus cannot transfer, at least in the distal fourth or third of the condom, from the exterior surface of the condom to the slip-resistant interior surface when the condom is rolled up. The condom of this embodiment may be worn for an extended period of time prior to intercourse, the thin secondary film layer being specifically designed to perform this function and to be readily removable at a suitable time prior to intercourse. (A further method of prelubricating condoms of this invention is discussed subsequently.)

The condom according to the present invention is optionally provided with 1) an increase in diameter toward the proximal, open end which defines a gradual taper along at least a substantial portion of the axial length, 2) an increasing diameter in the proximal direction along a portion of the axial dimension, thereby defining a substantially frusto-conical section which can terminate in a constant-diameter section near the open (proximal) end, 3) a small absorbent means which adhesively affixes to the interior tip of the condom, and optionally to the tip of a penis, 4) a small area of pressure-sensitive adhesive upon the tip of the interior surface of the condom, 5) a cap-like, secondary film layer of substantially conformal geometry between which secondary film layer and the contraceptive sheath is disposed a lubricant and/or biocide, spermicide, or other medicament, and 6) a secondary film layer which adhesively affixes to the exterior tip of the distal portion of the condom sheath, sealing a lubricant or other fluid therebetween.

Turning now to the Drawing, wherein like reference numerals denote like parts in the various views, FIG. 1 shows a perspective view of a generally cylindrical, sheath-like condom 10 of this invention having generally hemispherical distal or closed end 13 and proximal or open end 18. The generally tubular or cylindrical wall of condom 10 comprises slip-resistant interior surface 12 covered with outermost anti-blocking or release layer 14, which comprises the sheath material or which is anchored or adhered to the exterior of condom 10 and cannot transfer to interior 12 when condom 10 is rolled up in the conventional manner (as in FIG. 9, discussed below). The total thickness of the cylindrical wall of sheath-like condom 10, including release layer 14, is well within conventional limits (e.g., about 2 to about 4 mils or about 0.05 to about 0.10 mm), or even below conventional limits (e.g., 0.01 to 0.04 mm) but the principles of this invention can still be applied, if desired, to thicker sheaths (e.g., >0.15 mm in thickness). The rim 15 at open end 18 of condom 10 is substantially one to fifteen very tight convolutions of sheath material. During manufacture of condom 10, when the freshly-formed sheath is still on the dipping mandrel (not shown), rolling of rim 15 in the outward direction (i.e., outwardly onto the outer surface of condom 10) removes condom 10 from the dipping mandrel. During this rim-rolling step, interior surface 12 is rolled against release layer 14, thereby preventing the condom from adhering to itself, but release characteristics which could detract from the high coefficient of friction of interior surface 12 are not transferred to this surface.

The interior of closed end 13 of condom 10 optionally can contain absorbent means 22 and also can be seen in FIG. 6, which is an end elevation of condom 10 viewed from the open end 18 of this condom, but it is to be understood that the features shown in FIG. 6 also may be introduced into the closed end 13 of condoms 10A through 10D even though, for illustration purposes, it is shown only in FIG. 1. (FIG. 6 is discussed subsequently.)

Condoms 10A and 10B, shown in FIGS. 2 and 3, respectively, are based upon the same principles as condom 10 of FIG. 1 and are shown in the Drawing largely because of the findings of the noted researcher Alfred Kinsey who reported in detail on individual variations among human male genitalia including relationships between erect and flaccid penile size. A substantial number of individuals have a relatively large-diameter flaccid penis which expands primarily only in length when it becomes erect. Because condoms of this invention may be worn on a flaccid penis (in a partially unrolled condition), the larger annular ring of rolled convolutions near the base of the penis would be especially constricting for those individuals with a large-diameter flaccid penis. Condoms 10A and 10B of FIGS. 2 and 3, respectively, are much less constricting at the base of a flaccid penis than a straight tubular condom such as condom 10. A further advantage of the embodiments of FIGS. 2 and 3 is that condoms 10A and 10B optionally may have a greater axial length than commonly used in commercially-available condoms without sacrificing comfort. That is, a condom with a generally constant diameter in a partially unrolled condition will be strongly constricting at the proximal, open end and will normally have to be sized to approximate the "average" length of an erect penis (e.g., 150 mm), which is shorter than the penile length of a substantial number of individuals. However, the length of condoms 10A or 10B can accommodate comfortably a greater diversity of penile lengths. Even if condoms 10A and 10B are longer than "average", the resulting larger annular ring of rolled convolutions at the open end does not cause significant discomfort for the wearer, facilitates donning by providing additional surface area to be contacted by the fingers, and reduces the possibility of entanglement of body hair at the open end 18.

According to the embodiment of the condom shown in FIG. 2, condom 10A, there is provided a substantially gradually decreasing diameter along distance A, toward closed end 13. Stated another way, condom 10A tapers outwardly in the proximal direction along a portion of the axial length of condom 10A. FIG. 3 illustrates how a portion 17 of the condom 10B can be substantially frusto-conical in shape, due to a diameter dimension which increases proximally along axial distance B. But in both condom 10A of FIG. 2 and condom 10B of FIG. 3, close conformity to both the glans and a substantial portion of the shaft of a penis is still provided. Condom 10B is provided with a small bulbous region generally referred to as a receptacle end 33, which protrudes from closed end Receptacle end 33 also may be introduced into the condom structures of FIGS. 1, 2, 4 and 5 even though it is shown, for illustration purposes, only in FIG. 3.

In the embodiment shown in FIG. 4, condom 10C, the fundamental configuration and structure of condom 10C does not differ in principle from condom 10 (FIG. 1), but transfer of layer 21 (which can be a transferable film of liquid or solid lubricant or a transferable anti-blocking agent, i.e., a layer of material which is not anchored or adhered to the exterior of condom 10C, and/or a spermicide or other biocide or a medicament not anchored or adhered to the exterior of condom 10C) to interior surface 12 during roll-up is prevented by a thin, cap-shaped film structure 19 which conforms substantially to the geometry of and hence is superposed over approximately the distal fourth or distal third of the length of condom 10C, i.e., a third or fourth of the length of condom 10C extending proximally from closed end 13. As indicated previously, the portion of layer 21 which is protected from transfer by cap 19 can comprise a fluid such as a lubricant, spermicide, etc. The portion 21a of layer 21 which is not covered by cap 19, which will be transferred to interior surface 12 during roll-up, is not required to have biocidal, medicinal, or lubricant properties and can be strictly a release or dressing agent.

Cap 19, as indicated previously, preferably covers approximately the distal fourth to distal third of condom 10C, but can extend as little as 30 mm in the proximal direction or as much as 120 mm in this direction. For convenience of roll-up just prior to packaging of condom 10C, it is normally preferred that cap 19 not extend significantly more than 120 mm in the proximal direction, and in any event cap 19 preferably does not extend beyond layer 21 in the proximal direction, so that there is preferably always an uncovered portion 21a of layer 21, even if this portion 21a is only 5 or 10 mm in length.

Cap 19 is preferably thinner than sheath 10C. During manufacture of condom 10C, cap 19 is preferably preformed on and stripped from a slightly oversized dipping mandrel rather than formed in situ on a freshly-formed sheath coated with layer 21.

It is to be understood that cap 19 and layer 21 can be provided on other condom structures as well, e.g., condoms 10, 10A, and 10B, even though it is shown for illustration purposes only as part of the structure of condom According to the embodiment of FIG. 5, condom 10D the fundamental configuration and structure of condom 10D not differing in principle from condom 10 of FIG. 1, there is shown an alternative means of lubricating condom 10D by the provision of a substantially circular, flat or slightly convexed cap-like secondary layer 30 of approximately 20–30 mm in diameter and between about 0.03–0.40 mm in thickness. Secondary layer 30 adhesively affixes to the exterior tip of closed end 13 by means of a thin line of pressure-sensitive adhesive 29 of about 2–5 mm in width which is adjacent to the inside border along the entire circumference of peripheral edge 31 of the interior surface of secondary layer 30; thus, a fluid-resistant seal is formed between secondary layer 30 and the exterior tip of closed end 13. There is disposed a liquid such as a lubricant and/or biocide or other medicament 21 which is sealed between secondary layer 30 and the exterior of closed end 13, which liquid 21 is allowed to distribute upon the exterior surfaces of condom 10D following the removal of secondary layer 30. The outermost 2–5 mm of width about the entire circumference of the interior of secondary layer 30 forms peripheral edge 31, which peripheral edge 31 remains free from pressure sensitive adhesive, thereby facilitating easy removal of secondary layer 30 at a suitable time prior to intercourse. Secondary layer 30 is preferably fashioned from a material such as a gelatin, polyvinyl alcohol, or any other flexible non-sensitizing, biocompatable material which would not cause bodily harm if intercourse were initiated prior to its removal. It is to be understood that secondary layer 30 may be provided on other condom structures as well, e.g., 10A and 10B, even though it is shown for illustration purposes only as part of the structure of condom 10D.

Turning now to FIG. 6, which provides a view of the interior of closed end 13 and the remainder of the inside of condom 10 of FIG. 1 (but the features of FIG. 6 can also be introduced into the condom structures of FIGS. 2 through 5 even though it is shown, for illustration purposes, only in FIG. 1), there is provided in this region of the interior of closed end 13 an absorbent means 22 which is adhesively affixed to the tip of interior surface 12 of condom 10, which absorbent means 22 is positioned directly over the meatus (urethral opening) of a penis and prevents lubricious secretions of the cowpers and prostate glands from fluidly communicating with slip-resistant interior surface 12.

Absorbent means 22 which can be fashioned from any soft, absorbent, non-sensitizing material, is substantially circular in shape, more-or-less continuously formed, and is typically in the range of 10–30 mm in diameter; absorbent means 22 can be slightly larger .but does not extend proximally as far as the generally tubular or generally cylindrical portion of condom 10; that is, absorbent means 22 is confined substantially to the interior of generally hemispherical distal or closed end 13.

FIGS. 7 and 8 are views similar to that of FIG. 6 and provide illustrations of modifications of the features shown in FIG. 6. It is to be understood that the features shown in FIGS. 7 and 8 also could be introduced into a condom of any of the FIGS. 2 through 5 even though they are shown, for illustration purposes, only in FIG. 1.

FIG. 7 shows a modified absorbent means 23, similar in function to absorbent means 22 of FIG. 6, but provided with a toroidal shape having no absorbent material in centermost portion 24. The exposed posterior (proximal-facing) surface of absorbent means 23 is provided with pressure-sensitive adhesive coating 27 covering that surface substantially entirely, so that a pressure-sensitive adhesive bond can be formed, fixing absorbent means 23 to the tip (distal end) of a penis.

It is to be understood that the absorbent means 22 of the embodiment of FIG. 6 can also be provided with a coating of pressure-sensitive adhesive upon its exposed surface, in a manner closely analogous to coating 27 of FIG. 7.

According to FIG. 8, the interior of the distal end of condom 10 has been modified to omit substantially the absorbent means and simply provides a coating 25 of pressure-sensitive adhesive on the tip or closed end of interior surface 12 of the condom, which pressure-sensitive adhesive coating 25 is about 20 mm in diameter (or slightly larger, but in any event substantially confined to the curved interior of closed end 13) and is positioned to be directly over the urethral opening of a penis, thus preventing lubricious secretions of the cowpers and prostate glands from fluidly communicating with non-slip interior surface 12.

FIG. 9 illustrates a nearly fully rolled-up or convoluted condition of a condom of this invention, in this case condom 10 of FIG. 1. The tight spiral of convolutions 28, when viewed in cross-section, has the rim 15 of condom 10 at its center. It can be seen easily from FIG. 9 that release layer 14 prevents blocking of the interior of the convolutions, one upon the other, and when interior surface 12 comes into contact with the convoluted outer surface of condom 10, no transfer of release layer 14 onto surface 12 occurs.

When the rolled-up condition of condom 10 shown in FIG. 9 is completed, so that condom 10 is substantially entirely rolled into the plane of convolutions 28, condom 10 is in the best configuration for packaging and storage. After opening the packaged condom, centering it on the tip of a penis and beginning to unroll it over the glans of the penis, condom 10 will have the less-than-completely rolled-up configuration shown in FIG. 9.

Definition and Measurement of Properties

So-called "aggressive" or "permanent" tack, a property of pressure-sensitive adhesives, is a surface phenomenon which appears to be related to other forms of adhesion in that intermolecular forces may be involved (e.g., the formation of enormous numbers of weak hydrogen bonds between the adhesive and an adherend such as paper, wood, metal, etc.). Some amount of viscoelastic flow of solid adhesive onto or into the surface of the adherend may also be involved. The resulting pressure-sensitive adhesive bond resists peel forces. On the other hand, the chief causes of friction are the interlocking of the minute irregularities on the rubbing surfaces and, where applicable, indentation of the softer by the harder body, in addition to any adhesion that may occur. Thus, static and sliding friction would manifest themselves largely as shear-resistance forces and would not depend upon viscoelastic flow or intermolecular forces.

"Blocking" is a surface phenomenon normally considered to be a form of self-adherence, i.e., the tendency of sheets or films made of identical or similar material to stick together when their surfaces come into contact, even without pressing the surfaces together. Thus, a film surface which is "substantially non-blocking" will adhere negligibly to itself; in other words, a pair of films which are "substantially non-blocking" will either fail to stick to each other at all (with or without applied pressure) or will form such a slight adherent bond that they can be separated without application of measurable peel forces, e.g., by agitating the paired sheets in a liquid bath.

Various tests are available for measuring tacks e.g., the probe tack test (typically involving the use of a metal probe), 90° peel and 180° peel tests using a glass or metal substrate, and the like.

According to A.S.T.M. Designation D 2979-88, Standard Test Method for Pressure-Sensitive Tack of Adhesives Using an Inverted Probe Machine, a pressure-sensitive adhesive is "a viscoelastic material which in solvent-free form remains permanently tacky. Such material will adhere instantaneously to most solid surfaces with the application of very light pressure." Further, tack is defined as "the property of an adhesive that enables it to form a bond of measurable strength immediately after adhesive and adherend are brought into contact under low pressure."

Although the interior surface of the inventive condom has herein been described as slip-resistant and having a high coefficient of friction, when this surface is evaluated in accordance with A.S.T.M. D 2979-88, the tack (e.g., probe tack) of the interior surface of the condom of this invention is effectively unmeasurable.

This result is consistent with the objectives of this invention, which relate to frictional engagement of penile skin by 25 to 100%, preferably at least 50%, of the area of the internal surfaces of the condom, but which preferably do not include formation of an adhesive bond in the generally tubular or generally cylindrical portion of the condom which could impede or resist peeling of the condom film from penile skin which would cause an unpleasant sensation on the penile shaft or proximal glans during condom removal.

The coefficient of friction measurements herein reported are in accordance with A.S.T.M. Designation D 1894-90, Standard Test Method for Static and Kenetic Coefficients of Friction of Plastic Films and Sheeting. According to this standard, coefficient of friction is a measure of the relative difficulty with which the surface of one material will slide over an adjoining surface. The static coefficient of friction is related to the force measured to begin movement of the surfaces relative to each other.

The static coefficient of friction values (ASTM D 1894-90) set forth in the following Table 1 were obtained by measuring the material to be tested against itself, using various commercially-available condoms and several different condoms of this invention.

TABLE 1

ASTM D 1894-90 VALUES FOR CONDOMS

| Condom Tested | Coefficient of Friction* |
|---|---|
| Lady Protex ® Ultra Lubricated (Schmid Laboratories; silicone lubricant) | 0.54 |
| Beyond Seven ® Lightly Lubricated (Okamoto Industires, Incorporated; silicone lubricant) | 0.40 |
| Saxon ® Wet Lubricated (Safetex Corporation; water-based lubricant) | 0.47 |
| Trojan-Enz ® Lubricated (Carter-Wallace, Incorporated; water-based lubricant) | 0.48 |
| LifeStyles ® Non-Lubricated (Ansell Incorporated; dusting powder) | 0.39 |
| Trojan-Enz ® Non-Lubricated (Carter-Wallace, Incorporated, dusting powder) | 0.37 |
| Condoms of this invention | $\geq .70$ (e.g., 1.0–2.0) |

*These values represent the average of five (5) tests per condom type.

As is well known to persons knowledgeable in the physics of surface phenomena, the practical differences between a coefficient of friction of about 1.0 (or even 0.70) and a coefficient of friction of, for example, 0.54 are quite distinctly significant and readily apparent.

Thus, a condom of this invention provides significant advantages. The anti-slip interior surface of the inventive condom tends to grip the penile skin as the sheath is unrolled, thereby increasing the ease with which the condom is unrolled onto an erect penis. Because the condom may be worn for an extended time prior to intercourse upon either a flaccid or erect penis, lovemaking need not be interrupted as has generally been necessary with the use of condoms heretofore. Because the condom may be worn upon a flaccid penis, immediate withdrawal following ejaculation is not necessary; spillage does not occur. Due to the reduced slippage of the penis within the sheath, there is promoted a tactile relationship between the penis and vagina which more closely approximates the experience which occurs when no condom is being worn, thus providing increased physical sensation and pleasure for both parties. Because there is reduced movement of the penis within the contraceptive sheath, a "bunching-up" and/or creasing of material about the penis is eliminated. The contraceptive film of a contemporary, commercially-available condom which places a dressing agent in contact with the penis can be subject to a high degree of slippage, and excessive slippage results in substantial flexing which produces increased point stress. Slip-resistant condoms of this invention are therefore subject to reduced stress, resulting in a reduced incidence of breakage for the same or less sheath thickness as a condom which contacts the penis with a dressing agent.

The foregoing description of the preferred embodiments of this invention should be understood to be illustrative but non-limiting, since further embodiments or modifications of disclosed embodiments can be devised without departing from the principles of this invention.

What is claimed is:

1. A rolled contraceptive condom for a human penis in a rolled-up condition suitable for packaging, comprising:
   a sheath having, in the unrolled condition, a generally hemispherical closed, distal end, a generally tubular distal portion extending proximally from said closed distal end, and an open, proximal end, the generally tubular distal portion extending proximally to surround and fictionally engage an erect human penis when the condom is unrolled, said sheath having been rolled up outwardly upon itself, from said proximal end toward said distal end, the interior surfaces of at least said generally tubular distal portion being substantially free of any friction-reducing substance, being substantially free of measurable tack at an ambient temperature of about 40° C. and having, while the condom is in said rolled-up condition, a coefficient of static friction, as determined by ASTM Designation D 1894-90, which is >0.70; the material from which said sheath is comprised also having a said coefficient of static friction of >0.70.

2. A rolled condom according to claim 1, wherein the outermost surface of at least said distal portion is sufficiently non-blocking to prevent adherence to interior surfaces when the condom is rolled up.

3. A rolled condom according to claim 1, wherein said coefficient of static friction is at least about 1.0.

4. A rolled condom according to claim 20, wherein the outermost surface of at least said distal portion comprises a coating comprising an anti-blocking material deposited on said outermost surface of at least said distal portion, and said anti-blocking material is sufficiently adhered to said outermost surface to substantially prevent transfer of said anti-blocking material to the interior surfaces of said condom when said condom is rolled up or unrolled.

5. A rolled condom according to claim 1, wherein said sheath, when unrolled, has a length dimension which is long enough to envelop an erect adult human penis from its distal end to approximately its proximal end.

6. A rolled condom according to claim 5, wherein said distal portion of said condom is at least one-fourth of the unrolled length of said condom.

7. A rolled condom according to claim 6, wherein at least 50% of the area of the internal surfaces of said condom, extending proximally from the distal end, has said coefficient of friction, while the condom is in said rolled-up condition.

8. A rolled condom according to claim 1, wherein the exterior surface of at least said distal portion of said sheath is coated with a friction-reducing substance, and said friction-reducing substance has been inhibited from transfer to the internal surfaces of the sheath by application of a removable protective outer layer prior to said sheath having been rolled up upon itself.

9. A rolled condom according to claim 1, wherein said sheath, when unrolled, is elongated and has a diameter which increases generally uniformly in the proximal direction along at least a portion of its axial length.

10. A rolled condom according to claim 1, wherein said sheath, when unrolled, is, in the proximal direction, generally cylindrical and of generally uniform diameter to at least the proximal end of said distal portion, but which increases in diameter in the proximal direction, along at least a portion of the axial length of the condom.

11. A rolled condom according to claim 1, wherein the interior surface of said generally hemispherical closed, distal end is provided with a material for adhering said closed, distal end of the condom to the distal end of a penis, a material for absorbing pre-ejaculatory secretions from a penis, or a combination of said materials.

12. A rolled condom according to claim 1 which further comprises:

a cap-like secondary layer superposed upon a distal portion of the outer surface of said sheath and covering approximately at least the tip of the distal end but no more than about the distal third of said sheath, and a liquid lubricant, medicament, biocide, or combination thereof enclosed within at least some of the space between said secondary layer and the outer surface of said sheath.

13. A rolled condom according to claim 1, wherein the sheath has a wall thickness which is less than 0.15 mm.

14. A rolled contraceptive condom for a human penis in a rolled-up condition suitable for packaging, comprising:

a sheath having, in the unrolled condition, a generally hemispherical closed, distal end, a generally tubular distal portion extending proximally from said closed distal end, and an open, proximal end, the generally tubular distal portion extending proximally to surround and fictionally engage an erect human penis when the condom is unrolled, said sheath having been rolled up outwardly upon itself, from said proximal end toward said distal end, the interior surfaces of at least said generally tubular distal portion having deposited thereon a friction-enhancing substance, being substantially free of measurable tack at an ambient temperature of about 40° C. and having, while the condom is in said rolled-up condition, a coefficient of static friction, as determined by ASTM Designation D 1894-90, which is >0.70.

15. A rolled condom according to claim 14, wherein the outermost surface of at least the distal portion is sufficiently non-blocking to prevent adherence to interior surfaces when the condom is rolled up.

16. A rolled condom according to claim 14, wherein said coefficient of static friction is at least about 1.0.

17. A rolled condom according to claim 15, wherein the outermost surface of at least said distal portion comprises a coating comprising an anti-blocking material deposited on said outermost surface of at least said distal portion, and said anti-blocking material is sufficiently adhered to said outermost surface to substantially prevent transfer of said anti-blocking material to the interior surfaces of said condom when said condom is rolled up or unrolled.

18. A rolled condom according to claim 14, wherein said distal portion of said condom is at least one-fourth of the unrolled length of said condom.

19. A rolled condom according to claim 18, wherein at least 50% of the area of the internal surfaces of said condom, extending proximally from the distal end, has said coefficient of friction, while the condom is in said rolled-up condition.

20. A rolled condom according to claim 14, wherein the exterior surface of at least said distal portion of said sheath is coated with a friction-reducing substance, and said friction-reducing substance has been inhibited from transfer to the internal surfaces of the sheath by application of a removable protective outer layer prior to said sheath having been rolled up upon itself.

21. A rolled condom according to claim 14, wherein said sheath, when unrolled, is, in the proximal direction, generally cylindrical and of generally uniform diameter to at least the proximal end of said distal portion, but which increases in diameter in the proximal direction, along at least a portion of the axial length of the condom.

22. A rolled condom according to claim 14, wherein the interior surface of said generally hemispherical closed, distal end is provided with a material for adhering said closed, distal end of the condom to the distal end of a penis, a material for absorbing pre-ejaculatory secretions from a penis, or a combination of said materials.

23. A rolled condom according to claim 1 which further comprises:

a cap-like secondary layer superposed upon a distal portion of the outer surface of said sheath and covering approximately at least the tip of the distal end but no more than about the distal third of said sheath, and a liquid lubricant, medicament, biocide, or combination thereof enclosed within at least some of the space between said secondary layer and the outer surface of said sheath.

24. A rolled condom according to claim 14, wherein the sheath has a wall thickness which is less than 0.15 mm.

25. A rolled contraceptive condom for a human penis in a rolled-up condition suitable for packaging, comprising:

a sheath having, in the unrolled condition, a generally hemispherical closed, distal end, a generally tubular distal portion extending proximally from said closed distal end, and an open, proximal end, the generally tubular distal portion extending proximally to surround and fictionally engage an erect human penis when the condom is unrolled, said sheath having been rolled up outwardly upon itself, from said proximal end toward said distal end, the interior surfaces of at least said generally tubular distal portion having a friction-enhancing pattern thereon, being substantially free of measurable tack at an ambient temperature of about 40° C., and having, while the condom is in said rolled-up condition, a coefficient of static friction, as determined by ASTM Designation D 1894-90, which is >0.70, said coefficient of static friction being provided by said friction-enhancing pattern on said interior surfaces of at least said generally tubular distal portion.

26. A rolled condom according to claim 25, wherein the outermost surface of at least the distal portion is sufficiently non-blocking to prevent adherence to interior surfaces when the condom is rolled up.

27. A rolled condom according to claim 25, wherein said coefficient of static friction is at least about 1.0.

* * * * *